(12) United States Patent
Goldberg

(10) Patent No.: US 6,755,527 B1
(45) Date of Patent: Jun. 29, 2004

(54) TECHNIQUES FOR ANALYZING EYE MOVEMENTS

(75) Inventor: Joseph H. Goldberg, San Carlos, CA (US)

(73) Assignee: Oracle International Corporation, Redwood Shores, CA (US)

( * ) Notice: Subject to any disclaimer, the term of this patent is extended or adjusted under 35 U.S.C. 154(b) by 30 days.

(21) Appl. No.: 10/238,094

(22) Filed: Sep. 9, 2002

Related U.S. Application Data (60) Provisional application No. 60/340,146, filed on Dec. 14, 2001.

(51) Int. Cl.⁷ ................................................ A61B 3/14
(52) U.S. Cl. ...................................................... 351/209
(58) Field of Search ................................ 351/205, 209, 351/208, 210; 382/128; 345/629, 688, 7, 8, 9, 156, 157, 32; 600/300

(56) References Cited

U.S. PATENT DOCUMENTS

| | | | |
|---|---|---|---|
| 5,844,570 A | * | 12/1998 | Curtright et al. ........... 345/629 |
| 6,097,353 A | * | 8/2000 | Melville et al. ............... 345/8 |
| 6,421,064 B1 | * | 7/2002 | Lemelson et al. .......... 345/688 |

OTHER PUBLICATIONS

Gazetracker™: *Software Designed to Facilitate Eye Movement Analysis*, by Lankford, Chris, Dept. of Systems Engineering, Olsson Hall, University of Virginia, Charlottesville, VA 22903, © 2000 ACM ISBN 1–58113–280–8/00/0011.

* cited by examiner

*Primary Examiner*—George Manuel
(74) *Attorney, Agent, or Firm*—Hickman Palermo Truong & Becker LLP; Brian D. Hickman; Michael J. Meehan (57) ABSTRACT

Techniques are provided for receiving data associated with a user's eye movements when viewing an image. The received data is displayed in a tabular format on a first portion of a display device and displayed in a graphical format on a second portion of the display device.

35 Claims, 5 Drawing Sheets

TECHNIQUES FOR ANALYZING EYE MOVEMENTS

CROSS-REFERENCE TO RELATED APPLICATIONS

The present application claims priority to Provisional Patent Application Serial No. 60/340,146, filed Dec. 14, 2001, the disclosure of which is here by incorporated by reference herein in its entirety.

TECHNICAL FIELD

The systems and methods described herein relate to analyzing and displaying information associated with a user's eye movements when viewing an image.

BACKGROUND

Eye tracking studies are performed to evaluate particular design features of web sites, software applications, printed documents and other objects that are viewable by a user. Such eye tracking studies monitor a user's eye movements and record data such as fixation points, where the user's eye stops moving and fixates on a particular location on the web page or other image being viewed. During an eye tracking study, the coordinates of each fixation point and the duration of the fixation are recorded for later analysis.

The data collected during eye tracking studies can help identify portions of a web page or other image that attract a user's attention and identify other portions that do not attract the user's attention. Based on the results of one or more eye tracking studies, a web page or other image may be modified to attract the user's attention to the desired portion or portions of the web page or other image.

BRIEF DESCRIPTION OF THE DRAWINGS

The systems and methods described herein are illustrated by way of example, and not by way of limitation, in the figures of the accompanying drawings. Similar reference numbers are used throughout the drawings to reference similar elements and features.

DETAILED DESCRIPTION

The systems and methods described herein analyze and display information associated with a user's eye movements when viewing an image, such as a web page. For purposes of explanation, numerous specific details are set forth in order to provide a thorough understanding of the various systems and methods. It will be apparent, however, that the systems and methods described herein may be implemented without these specific details. The specification and drawings are, accordingly, to be regarded in an illustrative rather than a restrictive sense.

Particular examples are described herein with reference to one or more web pages viewed by a user. However, the systems and methods described herein may be applied to any type of image, whether produced on a computer display or on another object such as paper, cardstock, or any other material. Particular embodiments display the information associated with the user's eye movements in both a tabular format and a graphical format simultaneously. Different colors may be used to associate particular data displayed in the tabular format with the corresponding data displayed in the graphical format. The data may be analyzed to identify fixation points, scan paths, and one or more areas of interest. A particular embodiment identifies the fixation points and scan path and overlays the fixation points and scan path upon the image viewed by the user during an eye tracking study to identify the image information associated with the fixation points and the scan path.

Various types of systems are available to monitor a user's eye movements and record data associated with that eye movements. The systems and methods described herein that analyze and display information associated with the user's eye movements can be used with data from any number of eye monitoring systems. Many eye monitoring systems are currently available. Examples include Applied Science Laboratories (ASL) Model 504, the ERICA system available from ERICA Inc., and the EyeLink System available from SensoMotoric Instruments. However, the techniques described herein are not limited to any particular system for monitoring eye movements.

Exemplary Computer Display

Figure 1:
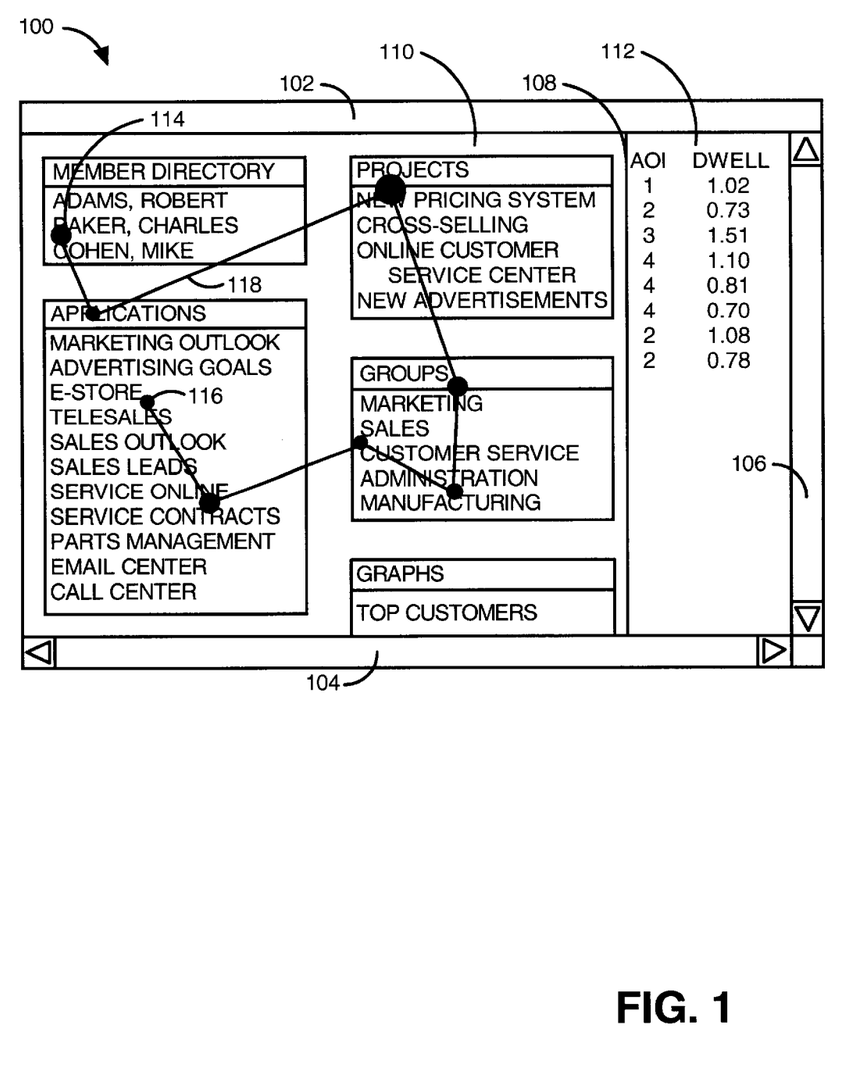
FIG. 1 illustrates an example computer display screen that is displaying a web page viewed by a user and data associated with a user's eye movements when viewing the web page.

FIG. 1 illustrates an example computer display screen 100 that is displaying a bitmap image of a web page viewed by a user during an eye tracking study and data associated with the user's eye movements during the eye tracking study. Computer display screen 100 includes a menu bar 102 that may contain any number of menu options, menu icons, or other information. A pair of scroll bars 104 and 106 allow the user of computer display screen 100 to change the information displayed on the screen by scrolling the information horizontally and/or vertically.

A vertical line 108 separates computer display screen 100 into two portions, a left portion 110 and a right portion 112. The left portion 110 of the screen displays the web site viewed by the user during the eye tracking study as well as fixation points 114 and 116 and a scan path 118 associated with the user's eye movements during the eye tracking study. The various fixation points are displayed as dots overlaying the image viewed by the user during the eye tracking study. The right portion 112 of the screen displays information associated with fixation points in tabular format. The information displayed in the right portion 112 of the screen includes an area of interest (abbreviated as "AOI") in which a particular fixation point is located and the amount of time (and possibly the percent of time) spent at each fixation point, referred to as the "Dwell" time, measured in seconds. An area of interest is an object or a region of the image viewed by the user that is of interest to the individual or organization analyzing the results of the eye tracking study. For example, computer display screen 100 includes five areas of interest: Member Directory, Applications, Projects, Groups and Graphs, numbered one through five, respectively. Alternate embodiments may include any number of areas of interest.

The scan path 118 is generated by connecting together the various fixation points in chronological order. The location and size of the fixation points are determined based on the data generated during the eye tracking study. The fixation points and the scan path 118 are graphical representations of the data generated during the eye tracking study. Similarly, the tabular data displayed in the right portion 112 of the display screen represents the same data generated during the eye tracking study in tabular form.

In the example of FIG. 1, scan path 118 begins at the first fixation point 114 in area of interest one (Member Directory), continues to a second fixation point in area of interest two (Applications), and so on until the scan path terminates at the last fixation point 116, also in area of interest two. Scan path 118 represents the visual path followed by a user's eyes while viewing the underlying web page during the eye tracking study. The eight entries in the right portion 112 of the screen correspond to the eight fixation points. For example, the first fixation point 114 is associated with area of interest one and has an associated dwell time of 1.02 seconds. The second fixation point is associated with area of interest two and has an associated dwell time of 0.73 seconds. The remaining six fixation points are listed in chronological order using the same format as the first two fixation points.

The size of each fixation point varies depending on the duration of the user's fixation at that point. The longer the duration of the user's fixation, the larger the associated fixation point. For example, the first fixation point 114 is larger than the last fixation point 116 because the duration of the user's fixation at the first fixation point (1.02 seconds) is longer than the user's fixation at the last fixation point (0.78 seconds).

Although FIG. 1 is not shown in color, the fixation points and various segments of the scan path 118 may be displayed in different colors along with the information displayed in the right portion 112 of the screen. For example, the first fixation point 114 and the corresponding first entry in the right portion 112 of the screen may be displayed in green. Green therefore indicates the starting point of the scan path 118. By coding both the first fixation point 114 and the corresponding entry in the right portion 112 of the screen the same color, the viewer of screen 100 can easily associate the fixation point with the appropriate tabular data. Similarly, the last fixation point 116 may be displayed in red along with the corresponding last entry in the right portion 112 of the screen. Red indicates the ending point of the scan path 118. The remaining six fixation points may be coded different colors (along with the corresponding tabular data) to more clearly associate the fixation points with the corresponding tabular data. Additionally, different segments of the scan path 118 may be displayed in different colors to distinguish the different segments from one another.

In a particular embodiment, the right portion 112 of the screen may display only a portion of the tabular data associated with the scan path and fixation points (i.e., the size of the tabular data exceeds the display capacity of the right portion of the screen). In this situation, when the viewer selects (using a mouse or similar device) a particular fixation point or a segment of the scan path, the tabular data associated with that fixation point or scan path segment is displayed in the right portion 112 of the screen. Thus, the tabular data that corresponds to the viewers selected fixation point or scan path segment is available for the viewer to analyze.

In alternate embodiments, instead of using different colors, different forms of highlighting, formatting and the like may be used to distinguish one fixation point from another. Such highlighting, formatting and the like may also be used to distinguish one scan path segment from another.

In other embodiments, the information displayed in the right portion 112 of the screen may include any information collected during the eye tracking study. Such alternate information includes the x and y coordinates of each fixation point, the name of the area of interest associated with each fixation point, or other data. In addition, the right portion 112 of the screen may display, for example, a transition matrix which shows the number and percentage of transitions between all pairs of AOIs, and/or statistical summaries that indicate whether the pattern of transition is random, or possibly directed in some way.

Although FIG. 1 illustrates a single vertical scroll bar 106, alternate embodiments may include multiple vertical scroll bars. For example, an additional scroll bar may be included within the left portion 110 of the screen, thereby allowing the left portion 110 of the screen to be scrolled independently of the right portion 112 of the screen. Similarly, multiple horizontal scroll bars may be provided in alternate embodiments.

Processing Data

Figure 2A:
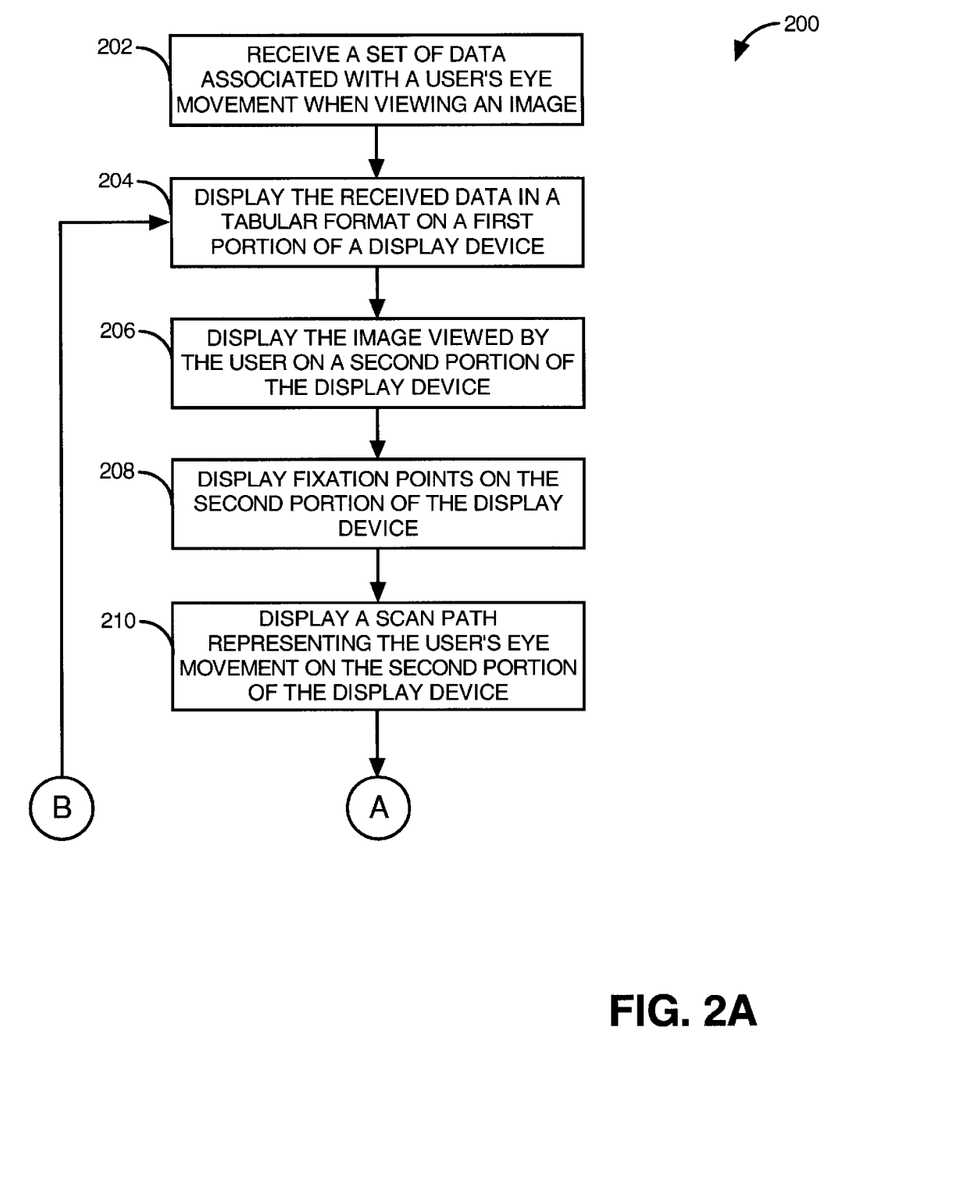
FIGS. 2A and 2B illustrate a flow diagram of a procedure for controlling the display of information associated with a user's eye movements when viewing an image.
Figure 2B:
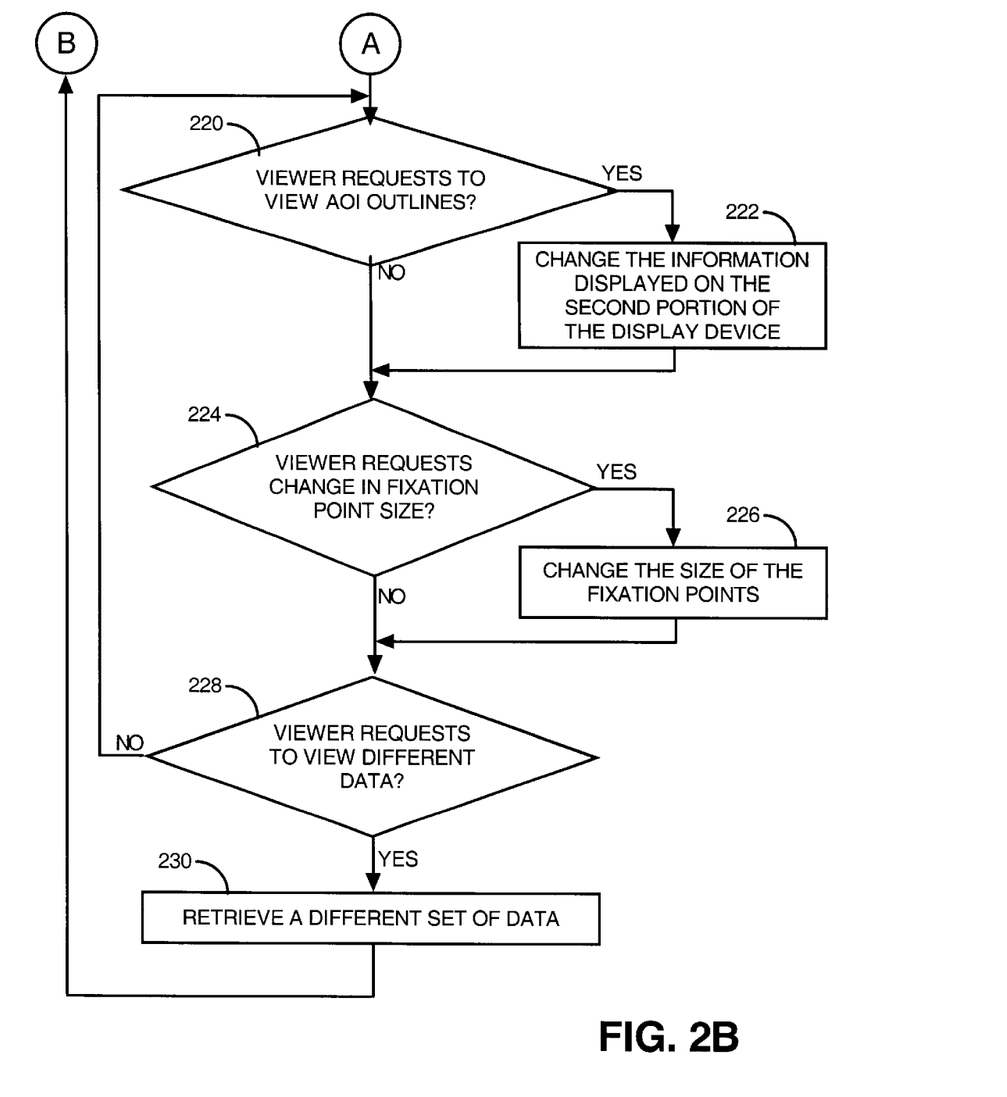

FIGS. 2A and 2B illustrate a flow diagram of a procedure 200 for controlling the display of information associated with a user's eye movements when viewing an image. Initially, the procedure 200 receives a set of data associated with a user's eye movements when viewing an image (block 202), such as a web page. The received data has typically been generated by a eye movements measuring system and recorded for later analysis. The received data is displayed in a tabular format on a first portion of a display device (block 204). For example, the tabular data can be displayed on the right portion 112 of computer display screen 100 discussed above with respect to FIG. 1.

The procedure 200 displays the image viewed by the user during the eye tracking study on a second portion of the display device (block 206). For example, the image viewed by the user can be displayed on the left portion 110 of computer display screen 100 discussed above with respect to FIG. 1. The procedure 200 also displays fixation points on the second portion of the display device (block 208). The fixation points are positioned such that their location corresponds to the portion of the underlying image the user was viewing at the time of the associated fixation. A scan path is also displayed on the second portion of the display device (block 210). The scan path connects the various fixation points in chronological order.

Procedure 200 continues to block 220 to determine whether the viewer has requested to view area of interest outlines. As mentioned above, areas of interest are objects or a region of the image that is of interest to the individual or organization analyzing the results of the eye tracking study. Area of interest outlines provide an outline around each area of interest but do not include the content contained in the area of interest, thereby simplifying the content of the display device. If the viewer has requested to view area of interest outlines at block 220, the procedure changes the information displayed on the second portion of the display device to include area of interest outlines instead of the full content of the area of interest (block 222).

The procedure 200 then determines whether a viewer has requested to change the size of the fixation points (block 224). A viewer may choose to increase the size of the fixation points to better see the differences in size between the different points. A viewer may also choose to decrease the size of the fixation points such that the points do not block as much of the underlying image. If the viewer has requested a change in the size of the fixation points, the appropriate change is made at block 226.

Procedure 200 next determines whether a viewer has requested to view a different set of data (block 228). For example, a viewer may request to view data associated with a different user that participated in the same eye tracking study. Alternatively, the viewer may request to view data associated with a different eye tracking study. If the viewer has made such a request, the different set of data is retrieved (block 230), and the procedure 200 returns to block 204 to display the new set of data. Otherwise, the procedure 200 returns to block 220 to check for other viewer requests to change the data displayed or the manner in which the data is displayed.

It should be noted that, while embodiments of the invention have been described where each display option is performed distinct and separate from the other options, other embodiments may display one or all options concurrently. For example, bitmaps, fixation data, AOI labels, and AOIs can all be simultaneously superimposed on a single display, and are no way mutually exclusive.

Alternate Display

Figure 3:
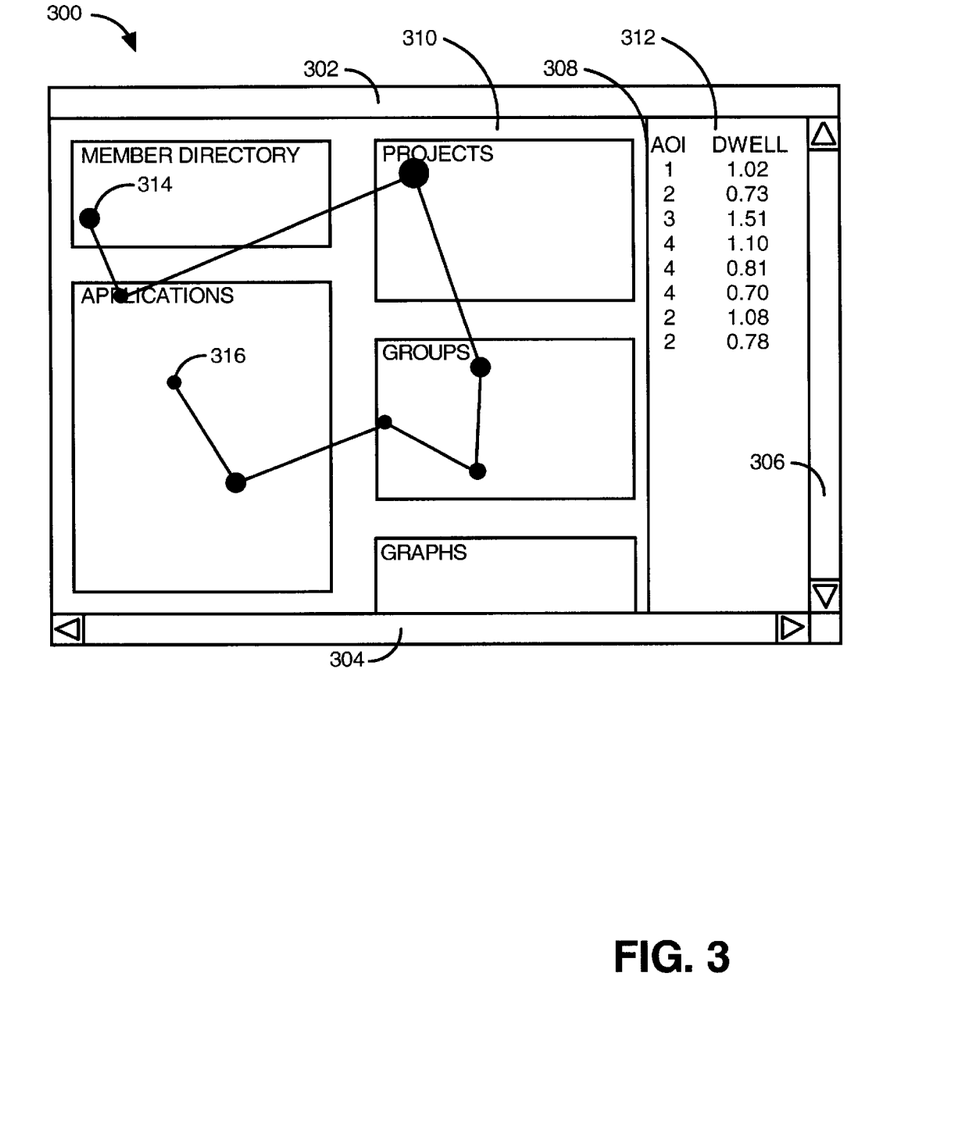
FIG. 3 illustrates an example computer display screen similar to the display screen shown in FIG. 1, but with less detail associated with each area of interest.

FIG. 3 illustrates an example computer display screen 300 similar to the display screen shown in FIG. 1, but with less detail associated with each area of interest. In the example of FIG. 3, each area of interest is shown with an outline and a label (or name) associated with the area of interest. The remaining information contained in the area of interest is deleted, thereby simplifying the display. The display shown in FIG. 3 corresponds with the resulting display if a viewer requests to view area of interest outlines at block 220 in FIG. 2.

Computer display screen 300 includes a menu bar 302 that can contain any number of menu options, menu icons, or other information. A pair of scroll bars 304 and 306 allow the user of computer display screen 300 to change the information displayed on the screen by scrolling the information horizontally and/or vertically.

A vertical line 308 separates computer display screen 300 into two portions, a left portion 310 and a right portion 312. The left portion 310 of the screen displays the web site viewed by the user during the eye tracking study as well as fixation points 314 and 316 and a scan path 318 associated with the user's eye movements during the eye tracking study. The right portion 312 of the screen displays information associated with fixation points and other information in tabular format. The information displayed in the right portion 312 of the screen includes an area of interest in which a particular fixation point is located and the amount of time spent at each fixation point; i.e., the "Dwell" time. The scan path 318 is generated by connecting together the various fixation points in chronological order. As mentioned above, the display may also include other types of information, such as, for example, a transition matrix which shows the number and percentage of transitions between all pairs of AOIs, and/or statistical summaries that indicate whether the pattern of transition is random, or possibly directed in some way.

Hardware Overview

Figure 4:
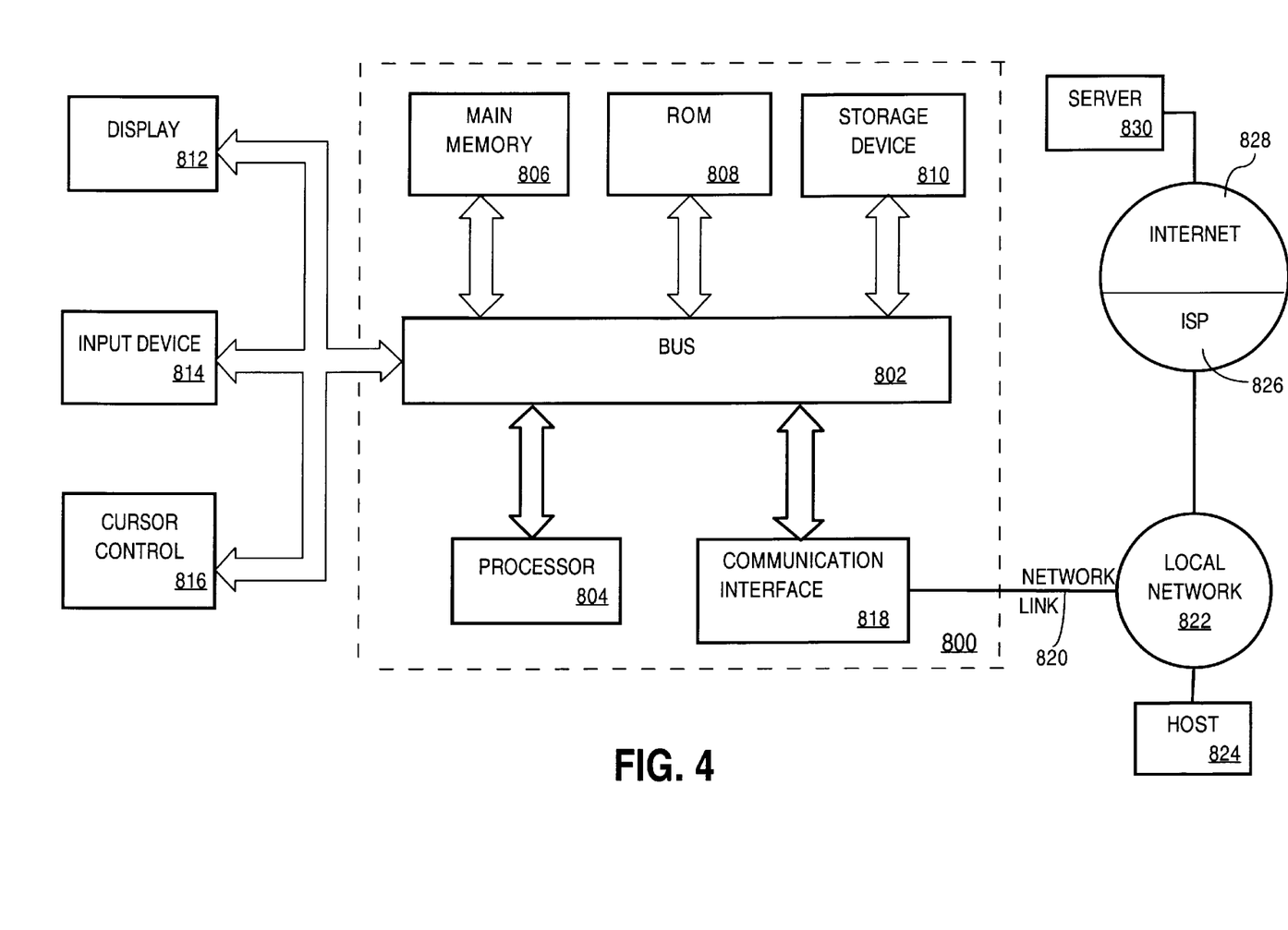
FIG. 4 is a block diagram that illustrates a computer system upon which the procedures discussed herein may be implemented.

FIG. 4 is a block diagram that illustrates a computer system 400 upon which the procedures discussed herein may be implemented. Computer system 400 includes a bus 402 or other communication mechanism for communicating information, and a processor 404 coupled with bus 402 for processing information. Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Computer system 400 further includes a read only memory (ROM) 408 or other static storage device coupled to bus 402 for storing static information and instructions for processor 404. A storage device 410, such as a magnetic disk or optical disk, is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

The described systems and methods are related to the use of computer system 400 for implementing various techniques described herein. According to one embodiment, those techniques are performed by computer system 400 in response to processor 404 executing one or more sequences of one or more instructions contained in main memory 406. Such instructions may be read into main memory 406 from another computer-readable medium, such as storage device 410. Execution of the sequences of instructions contained in main memory 406 causes processor 404 to perform the process steps described herein. In alternative embodiments, hard-wired circuitry may be used in place of or in combination with software instructions to implement the systems and methods described herein. Thus, the described systems and methods are not limited to any specific combination of hardware circuitry and software.

The term "computer-readable medium" as used herein refers to any medium that participates in providing instructions to processor 404 for execution. Such a medium may take many forms, including but not limited to, non-volatile media, volatile media, and transmission media. Non-volatile media includes, for example, optical or magnetic disks, such as storage device 410. Volatile media includes dynamic memory, such as main memory 406. Transmission media includes coaxial cables, copper wire and fiber optics, including the wires that comprise bus 402. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 404 for execution. For example, the instructions may initially be carried on a magnetic disk of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are exemplary forms of carrier waves transporting the information.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution. In this manner, computer system 400 may obtain application code in the form of a carrier wave.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A method comprising:
   receiving data generated by monitoring a user's eye movements when viewing an image;
   displaying the received data in a tabular format on a first portion of a display device; and
   displaying the received data in a graphical format on a second portion of the display device.

2. The method of claim 1 wherein one of said first portion and said second portion is superimposed over the other of said first portion and said second portion.

3. The method of claim 1 wherein displaying the received data in a graphical format on a second portion of the display device includes analyzing the received data to determine a scan path associated with the user's eye movements.

4. The method of claim 1 wherein the data displayed in the tabular format is color-coded to match the corresponding data displayed in the graphical format.

5. The method of claim 1 wherein the data displayed in the graphical format includes a plurality of areas of interest associated with the image viewed by the user when the data generated by monitoring the user's eye movements was recorded.

6. The method of claim 1 wherein the data displayed in the tabular format includes coordinates associated with a plurality of fixation points.

7. The method of claim 1 further comprising allowing a user to change a level of detail presented in the graphical format.

8. The method of claim 1 wherein selecting a particular area of interest causes the corresponding tabular data to be displayed on the first portion of the display device.

9. The method of claim 1 wherein the tabular data includes information associated with areas of interest.

10. The method of claim 9 wherein the information associated with areas of interest includes a dwell time for each area of interest.

11. The method of claim 9 wherein the information associated with areas of interest includes a percentage of time that the user's eye dwelt on each area of interest.

12. The method of claim 1 wherein the data in graphical format includes a graphical display of a plurality of fixation points, and the tabular data includes information associated with each of said fixation points.

13. The method of claim 12 wherein the graphical display associated with each fixation point is displayed in a color that
   is different than the color used to display the other of said plurality of fixation points, and
   corresponds to a color used to display the information associated with said fixation point.

14. The method of claim 12 wherein the graphical display associated with each fixation point is displayed in a particular manner that
   is different than the manner used to display the other of said plurality of fixation points, and
   corresponds to a manner used to display the information associated with said fixation point;
   wherein the manner includes one or more of color, highlighting and formatting.

15. The method of claim 1 further comprising the step of displaying information about a pattern of transition of said eye movements.

16. A method comprising:
   receiving data generated by monitoring a user's eye movements when viewing an image;
   displaying the received data in a tabular format on a first portion of a display device, wherein data associated with a first area of interest is displayed in a first color, and data associated with a second area of interest is displayed in a second color; and
   displaying the received data in a graphical format on a second portion of the display device, wherein the first area of interest is displayed in the first color and the second area of interest is displayed in a second color.

17. The method of claim 16 wherein the first area of interest is associated with an area of user fixation.

18. The method of claim 16 wherein the data displayed in the graphical format includes a plurality of areas of interest associated with the image viewed by the user when the data generated by monitoring the user's eye movements was recorded.

19. A computer-readable medium carrying instructions which, when executed by one or more processors, cause the one or more processors to perform the steps of:
   receiving data generated by monitoring a user's eye movements when viewing an image;
   displaying the received data in a tabular format on a first portion of a display device; and
   displaying the received data in a graphical format on a second portion of the display device.

20. The computer-readable medium of claim 19 wherein displaying the received data in a graphical format on a second portion of the display device includes analyzing the received data to determine an area of interest.

21. The computer-readable medium of claim 19 wherein the data displayed in the tabular format is color-coded to match the corresponding data displayed in the graphical format.

22. The computer-readable medium of claim 19 wherein the data displayed in the graphical format includes a plurality of areas of interest associated with the image viewed by the user when the data generated by monitoring the user's eye movements was recorded.

23. The computer-readable medium of claim 19 wherein the data displayed in the tabular format includes coordinates associated with a plurality of fixation points.

24. The computer-readable medium of claim 19 further comprising instructions for allowing a user to change a level of detail presented in the graphical format.

25. The computer-readable medium of claim 19 wherein selecting a particular area of interest causes the corresponding tabular data to be displayed on the first portion of the display device.

26. The computer-readable medium of claim 19 wherein the tabular data includes information associated with areas of interest.

27. The computer-readable medium of claim 26 wherein the information associated with areas of interest includes a dwell time for each area of interest.

28. The computer-readable medium of claim 26 wherein the information associated with areas of interest includes a percentage of time that the user's eye dwelt on each area of interest.

29. The computer-readable medium of claim 19 wherein the data in graphical format includes a graphical display of a plurality of fixation points, and the tabular data includes information associated with each of said fixation points.

30. The computer-readable medium of claim 29 wherein the graphical display associated with each fixation point is displayed in a color that
   is different than the color used to display the other of said plurality of fixation points, and
   corresponds to a color used to display the information associated with said fixation point.

31. The computer-readable medium of claim 29 wherein the graphical display associated with each fixation point is displayed in a particular manner that
   is different than the manner used to display the other of said plurality of fixation points, and
   corresponds to a manner used to display the information associated with said fixation point;
   wherein the manner includes one or more of color, highlighting and formatting.

32. The computer-readable medium of claim 19 further comprising instructions for performing the step of displaying information about a pattern of transition of said eye movements.

33. A computer-readable medium carrying instructions which, when executed by one or more processors, cause the one or more processors to perform the steps of:
   receiving data generated by monitoring a user's eye movements when viewing an image;
   displaying the received data in a tabular format on a first portion of a display device, wherein data associated with a first area of interest is displayed in a first color, and data associated with a second area of interest is displayed in a second color; and
   displaying the received data in a graphical format on a second portion of the display device, wherein the first area of interest is displayed in the first color and the second area of interest is displayed in a second color.

34. The computer-readable medium of claim 33 wherein the first area of interest is associated with an area of user fixation.

35. The computer-readable medium of claim 33 wherein the data displayed in the graphical format includes a plurality of areas of interest associated with the image viewed by the user when the data generated by monitoring the user's eye movements was recorded.

* * * * *